United States Patent
Protasiewicz et al.

(10) Patent No.: US 9,433,526 B2
(45) Date of Patent: Sep. 6, 2016

(54) CUTANEOUS PROPRIORECEPTIVE ACTIVATION GARMENT SYSTEM

(75) Inventors: Rich Protasiewicz, Wauwatosa, WI (US); William Anderson, West Allis, WI (US); Gail Nichols, Bluffton, SC (US)

(73) Assignee: Perfect Cross, LLC, Nashotah, WI (US)

( * ) Notice: Subject to any disclaimer, the term of this patent is extended or adjusted under 35 U.S.C. 154(b) by 295 days.

(21) Appl. No.: 12/435,352

(22) Filed: May 4, 2009

(65) Prior Publication Data

US 2010/0049112 A1  Feb. 25, 2010

Related U.S. Application Data

(60) Provisional application No. 61/050,135, filed on May 2, 2008.

(51) Int. Cl.
| A61F 13/02 | (2006.01) |
| A61F 7/02 | (2006.01) |
| A61F 5/01 | (2006.01) |

(52) U.S. Cl.
CPC .............. *A61F 7/02* (2013.01); *A61F 5/0104* (2013.01); *A61F 5/0106* (2013.01); *A61F 5/0111* (2013.01); *A61F 5/0118* (2013.01); *A61F 13/02* (2013.01); *A61F 13/0273* (2013.01); *A61F 2007/0233* (2013.01)

(58) Field of Classification Search
CPC .... A61F 13/00; A61F 13/02; A61F 13/0273; A61F 13/06; A61F 13/062; A61F 5/058; A61F 5/05825; A61F 5/05841; A61F 5/0585; A61F 5/05858; A61F 5/08

USPC .............. 602/5, 26, 60–62, 23, 75, 54; 2/69; 482/121, 124; 523/105, 111, 113; 606/199

See application file for complete search history.

(56) References Cited

U.S. PATENT DOCUMENTS

| 3,934,583 A | 1/1976 | Hollingshead et al. |
| 4,702,234 A | 10/1987 | Huntjens |
| 4,724,831 A | 2/1988 | Huntjens |

(Continued)

FOREIGN PATENT DOCUMENTS

| EP | 1561446 | 8/2005 |
| EP | 1810649 | 7/2007 |

(Continued)

OTHER PUBLICATIONS

PCT International Search Report and Written Opinion for Application No. PCT/US2009/042752 dated Jun. 17, 2009 (8 pages).

(Continued)

*Primary Examiner* — Keri J Nelson
(74) *Attorney, Agent, or Firm* — Michael Best & Friedrich LLP

(57) ABSTRACT

An appliance for application to the human body for injury prevention, rehabilitation, support, to enhance strength, and to improve posture. The claimed invention may provide an applicator of a relatively elastic material having a first portion for attachment to a first insertion point of a muscle and a second portion for attachment to a second insertion point of the muscle to provide support to the injured muscle. Alternatively, the claimed invention may provide a central portion for attachment to an injured area and any number of extension portions for attachment to the surrounding tissue.

9 Claims, 13 Drawing Sheets

(56) References Cited

U.S. PATENT DOCUMENTS

| | | | |
|---|---|---|---|
| 5,144,694 A | 9/1992 | Conrad Da oud et al. | |
| 5,263,923 A | 11/1993 | Fujimoto | |
| 5,367,708 A | 11/1994 | Fujimoto | |
| 5,555,562 A | 9/1996 | Holt et al. | |
| 5,582,583 A | 12/1996 | Ballantyne | |
| 5,584,799 A * | 12/1996 | Gray | A61F 5/05866 602/18 |
| 5,606,745 A * | 3/1997 | Gray | 2/69 |
| 5,640,714 A | 6/1997 | Tanaka | |
| 5,745,917 A | 5/1998 | Dicker et al. | |
| 5,782,790 A | 7/1998 | Allen | |
| 5,799,328 A | 9/1998 | Harlem et al. | |
| 5,823,851 A | 10/1998 | Dicker | |
| 5,829,058 A | 11/1998 | Dicker et al. | |
| 6,086,551 A | 7/2000 | Allen | |
| 6,186,970 B1 | 2/2001 | Fujii et al. | |
| 6,258,014 B1 | 7/2001 | Karecki | |
| 6,428,495 B1 | 8/2002 | Lynott | |
| 6,430,752 B1 | 8/2002 | Bay | |
| 6,446,264 B2 | 9/2002 | Fairhurst et al. | |
| 6,506,957 B1 | 1/2003 | Himmelsbach et al. | |
| 6,768,039 B1 * | 7/2004 | Beaudry | A61F 5/08 602/42 |
| 6,849,057 B2 * | 2/2005 | Satou et al. | 602/75 |
| 7,074,204 B2 | 7/2006 | Fujii et al. | |
| 7,153,246 B2 | 12/2006 | Koscielny et al. | |
| 7,156,792 B2 | 1/2007 | Gibson-Horn | |
| 7,229,390 B2 | 6/2007 | Fujii et al. | |
| 2001/0027282 A1 | 10/2001 | Baugh | |
| 2002/0091348 A1 | 7/2002 | Joseph | |
| 2002/0147422 A1 | 10/2002 | Darcey et al. | |
| 2003/0069530 A1 | 4/2003 | Satou et al. | |
| 2003/0139698 A1 * | 7/2003 | Hyson | 602/61 |
| 2004/0255358 A1 | 12/2004 | Ota et al. | |
| 2005/0193461 A1 | 9/2005 | Caillibotte et al. | |
| 2006/0000478 A1 | 1/2006 | Taylor | |
| 2006/0030802 A1 * | 2/2006 | Nordt et al. | 602/26 |
| 2006/0046913 A1 | 3/2006 | Spuittieri | |
| 2006/0064794 A1 | 3/2006 | Howard et al. | |
| 2006/0130215 A1 | 6/2006 | Torry | |
| 2006/0169004 A1 | 8/2006 | Belluye et al. | |
| 2006/0240953 A1 | 10/2006 | Shahinpoor | |
| 2007/0111868 A1 | 5/2007 | Fuji et al. | |
| 2007/0135279 A1 | 6/2007 | Purdy et al. | |
| 2007/0155522 A1 | 7/2007 | Kim | |
| 2007/0179421 A1 | 8/2007 | Farrow | |
| 2007/0214541 A1 | 9/2007 | Kawasaki et al. | |
| 2007/0235139 A1 | 10/2007 | Kawahara | |
| 2007/0299380 A1 | 12/2007 | Salivonchik et al. | |

FOREIGN PATENT DOCUMENTS

| | | |
|---|---|---|
| JP | 4050302 | 2/1992 |
| JP | 09-031720 | 2/1997 |
| JP | 10-146375 | 6/1998 |
| JP | 2003-293206 | 10/2003 |
| JP | 2004-49541 | 2/2004 |
| JP | 2004-263362 | 9/2004 |
| JP | 2005-048332 | 2/2005 |
| JP | 2005-146450 | 9/2005 |
| WO | WO 2005/115558 A2 | 12/2005 |
| WO | WO 2006/032096 A1 | 3/2006 |
| WO | WO 2006/043476 | 4/2006 |
| WO | WO 2007/036751 A2 | 4/2007 |
| WO | WO 2008101314 A1 * | 8/2008 |
| WO | WO 2008/122873 A1 | 10/2008 |
| WO | WO 2008/127929 A1 | 10/2008 |

OTHER PUBLICATIONS

Canadian Patent Office Examination Report for Application No. 2723312 dated May 28, 2015 (5 pages).

Extended European Search Report for Application No. 09740024.6 dated Dec. 3, 2015 (6 pages).

Canadian Patent Office Examiner's Report for Application No. 2723312 dated Feb. 10, 2016 (6 pages).

* cited by examiner

CUTANEOUS PROPRIORECEPTIVE ACTIVATION GARMENT SYSTEM

PRIORITY CLAIM

This application claims the benefit of U.S. Provisional Application No. 61/050,135 May 2, 2008.

FIELD OF THE INVENTION

The claimed invention relates to a device applied to the skin of a human being or an animal for therapeutic purposes. More specifically, the claimed invention relates to a device applied to an area of the body for injury prevention, rehabilitation and support, among other benefits to be discussed in the following disclosure.

BACKGROUND OF THE INVENTION

Generally, two types of injury trauma exist, those caused by force and those caused by overuse. Force traumas cause injuries in which an individual receives an acute injury to body tissues. Examples of force traumas include: broken bones, dislocations, muscle bruises, blunt trauma, sprains, and other wounds. Overuse injuries are caused by repetitive overuse of certain body tissues resulting in microscopic tissue injury. Generally, the body is not allowed adequate time to heal because the individual fails to adequately recover from continually repeated movement or prior workouts. As a result, minor injuries are aggravated into more serious injuries. Examples of overuse injuries include: shin splints, tendonitis, carpal tunnel injuries, and stress fractures. Pathology and disease states such as arthritis, lupus, degenerative muscle disorders may also cause or result in injury to tissues and pain.

Injuries are generally classified as acute or chronic. An acute injury is a recent injury that occurred as a result of a traumatic event or action. Acute injuries include: muscle pulls, ligament sprains, fractures, dislocations, contusions and bruises, among other things. Chronic injuries occur as a result of overuse or a long-standing condition. Chronic injuries seen in orthopedics include: overuse syndromes, tendonitis, bursitis and arthritis. Overuse syndromes, also called cumulative trauma disorder (CTD) or repetitive strain injury (RSI), are conditions characterized by chronic irritation to a body part. Many conditions fall within the category of overuse syndromes.

"Tissue" refers to soft tissue, muscle tissue, bone tissue, tendons, ligaments and cartilage among other things. In general, the healing process for traumatized tissue follows a specific physiological sequence. Within the first 24 hours, a series of vascular, cellular and chemical events occur following an initial trauma. Immediately following an injury that is, during the acute phase, blood flow to the injury site increases. Blood vessels, broken during injury, are sometimes not able to contain the blood flow to the injured area. As a result blood spills into the injured area, causing inflammation, or more commonly, swelling, of the area. There are two primary causes of pain in injuries, (1) a nerve ending sending an impulse to the brain and (2) inflammation causing nerve endings to be stretched and send an impulse to the brain.

There are certain factors that impede tissue healing. The nature or the amount of the inflammatory response is determined by the extent of the tissue injury. Edema impedes tissue healing because the increased pressure caused by swelling retards the healing process, causes separation of tissues, inhibits neuromuscular control, produces reflexive neurological changes and impedes nutrition to, and waste removal from, the injured area. Bleeding, or hemorrhage, occurs with even the smallest amount of damage to the capillaries which can add to further inflammation. Additional inflammation adds more pressure and pain to the injured area.

Vascular supply to the area has an effect on healing and also has an effect on the healing process. Injuries to tissues with a poor vascular supply heal poorly and at a slower rate. For example, injuries to tendons and ligaments, in general, heal more slowly because they have low vascular supply. The type of tissue injury can also affects the healing process. In general, mechanically separated, smooth edges heal better and more quickly than jagged edged damaged tissue. Muscle spasms in the injured area may also affect healing as traction on torn tissue prevents approximation of the injured edges of the tissue. Atrophy, the wasting away of muscle tissue, begins immediately with trauma. Oxygen tension relates to the neovascularization of the wound. Optimal saturation with oxygen is required for the return of maximal tensile strength and development. Of course, the health, age and nutrition intake of the individual will also affect the healing capacity of the body to the injury. Acute injuries become chronic injuries when the body ceases to be able to cope with the tissue destruction, edema, and/or continued overuse. Pain and swelling continues at rest and the movement or joint motion remains suboptimal for days to months or more.

A joint is the location at which two or more bones come together within the anatomical structure. Joints allow movement and provide mechanical support. Joints are mainly classified structurally and functionally.

Structural classification is determined by how the bones connect to each other. There are three structural classifications of joints. A fibrous joint is joined by fibrous connective tissue, while a cartilaginous joint is joined by cartilage. Synovial joints are not directly joined.

Functional classification is determined by the degree of movement between the articulating bones and the amount of mobility that they allow. A synarthrosis joint permits little or no mobility. Most synarthrosis joints are fibrous joints, such as those, for example, in the skull. An amphiarthrosis joint permits slight mobility. Most of these joints are cartilaginous joints, for example, vertebrae. A diarthrosis joint permits a variety of movements. All diarthrosis joints are synovial joints. Such joints include the shoulder, hip, elbow and knee. A diarthrosis and a synovial joint are considered equivalent.

Joints can also be classified based on their biomechanical properties. Biomechanically, joints are subdivided into simple, compound and complex. Simple joints have two articulating surfaces, such as the shoulder and the hip. Compound joints such as the radiocarpal, or wrist joint, have 3 or more articulating surfaces. A complex joint such as the knee has 2 or more articulating surfaces and an articular disc or meniscus.

With the foregoing basic understanding of anatomy and physiology, one recognizes that joint and muscle mechanics are interconnected. Bones are required for movement and locomotion, but they are unable to move on their own. They must be moved by the alternate contraction and relaxation of the skeletal muscles. Skeletal muscles (also known as striated, voluntary muscles and skeletal muscle) act on the bones that serve as a system of levers. Voluntary muscles control the movement that you have direct control over. These muscles are responsible for making almost any movement that is required. Voluntary muscles are also found in your face and jaws, so they are used when you smile or frown and when you talk, eat or drink.

Joints are the points at or around which the bones move to create motion. Many bones have ridges and protuberances which provide an area for muscle attachment. Muscles may move the whole body, or part of it, or some material along a tube within it. That is, movement does not depend on movement from only one joint (location). Specific joint stability is not solely dependant on the stability of that specific joint alone. This being said, injuries to one joint affect other joints and musculature and therefore the support and rehabilitation of anatomy, and training for a certain action, often requires rehabilitation and training of other areas of the body, often in conjunction with the perceived injured joint and musculature.

For every muscle or group of muscles that bring about movement of a certain part of the body, there is another muscle, or group of muscles, which bring about an opposite movement. All muscles work in pairs. This is because muscles can contract and relax but cannot push or stretch themselves. Muscles that bring about opposite movements are called antagonistic muscles. As the one muscle contracts, the other relaxes, and vice versa. The antagonistic action allows the smooth coordination of movement possible. When a muscle is stimulated it contracts and becomes shorter and thicker thus moving the bone to which it is attached. When it is relaxed, the muscle becomes longer and thinner. For example, in moving one's arm, when the biceps contracts it flexes the elbow joint. At the same time it also pulls the triceps to make it longer. So the triceps is stretched by the biceps pulling it. When the triceps contracts it extends the arm and at the same time it pulls the biceps and makes it longer. So these two muscle groups work together, antagonistically. Movement is brought about by muscles doing work by pulling as they contract. No work is done by a muscle pushing as it elongates.

The functional element of striated muscle is the muscle fiber, which has many fine threads or myofibrils running throughout its length. After nervous stimulation, electrical changes in the membrane surrounding each myofibril cause the release of calcium ions which results in muscle shortening. Oxygen is carried to muscles by the blood, which runs in a plexus of fine capillaries in between the fibers. Waste products such as carbon dioxide and lactic acid are carried away in the blood.

The nerve supply to a striated muscle usually enters along with the blood vessels. The nerve to a muscle is mixed, that is it contains both motor fibers which convey impulses from the spinal cord to the muscle and sensory fibers which relay information back to the spinal cord. The motor fibers branch within the muscle, and one nerve cell supplies several muscle fibers distributed throughout the muscle. Each muscle fiber receives only one terminal branch of a nerve fiber at the neuromuscular junction.

The signal is passed between the two cell membranes, that of the nerve fiber (called the pre-synaptic membrane) and that of the muscle cell (called the post-synaptic membrane). A wave of depolarization (movements of sodium and potassium ions) along the fiber releases calcium ions and initiates the process of contraction.

A sensory receptor is a part of a sensory neuron or cell that receives information from the world and relates it to the nervous system. There are several different types of sensory neurons within the body. For example, Pacinian corpuscles in the skin are the deep pressure receptors. Some outside force has to have a way to act on the sensory nerve. In the case of the Pacinian corpuscle, a very forceful pressing on the skin activates it. Mechanoreceptors respond to mechanical stress or mechanical strain. Muscle spindles contain mechanoreceptors that detect stretch in muscles. Nociceptors respond to damage to body tissues leading to pain perception. Thermoreceptors respond to temperature, either heat, cold or both. Cutaneous receptors are sensory receptors found in the dermis or epidermis. Proprioceptors provide the sense of position.

Within and around a joint are many structures required to allow function of that structure. There are many muscles and tendons, which insert or originate on the distal end of the femur or proximal end of the tibia and fibula and cover and support the patella. The femur, tibia and patella are the bones that create the knee joint. There are ligaments that hold bone to bone and cartilage is at the distal and proximal ends of the bone to cushion areas of bone to withstand force and to protect the bone from wear and tear. A bursa is a small fluid filled sac or saclike cavity situated in places in tissues where friction would otherwise occur. Bursae function to facilitate the gliding of skin, muscles or tendons over bony or ligamentous surfaces. They are numerous and are found throughout the body; the most important are located at the shoulder, elbow, knee and hip. Inflammation of a bursa is known as bursitis. Synovium is the smooth lining of a joint. A flexible joint is lined by a synovial membrane. Synovium produces synovial fluid (illustration), a clear substance that lubricates and nourishes the cartilage and bones inside the joint capsule. Injury to any of these structures (muscle, tendon, ligament, cartilage, meniscus, bursa or synovium) can result in pain. There are two menisci in your knee. The medial meniscus is on the inside of the knee while the lateral meniscus is on the outside of the knee. Each meniscus rests between the thigh bone (femur) and shin bone (tibia). The menisci are made of tough cartilage and conform to the surfaces of the bones upon which they rest. These menisci function to distribute the body weight across the knee joint. If the meniscus was not present, the body weight would be unevenly applied to the bones in the legs (femur and tibia).

Relative strength differences between ligament and bone can predict the location of injury within the joint. In pediatric patients, the ligament is generally strongest at the growth plate or the bone is weakest at the growth plate. When there is stress on the joint, injury is likely to occur at the growthplate. With an adult, bone is normally stronger than the structure of the ligament. As a result, in an adult, ligaments rupture first. In geriatrics patients, the ligament is stronger than the bone. As a result, frequently, the bone will fracture first.

Sprains occur when there is a tear to a ligament. Grade I sprains result from stretching of the ligament or a minor tear of the ligament. There is no laxity of the ligament. Grade II sprains are a result of an incomplete tear. Laxity of the ligament is evident and there is usually swelling associated with the injury. A Grade III sprain is characterized by a complete tear of the ligament. There is increased laxity of the ligament with swelling (edema). The individual is definitely experiencing pain.

The most common cause of joint pain is overuse and/or repetitive motion. Certain types of athletic activities employ repetitive motion. Other repetitive motion pain and injury occurs through simple use of a joint over time. Overuse injuries are also frequently work-related injuries associated with continued repetitive motion such as typing, working with tools and other simple repetitive motions.

Overuse injuries are caused in two basic ways. In the first scenario, the movement is inconsistent with the anatomy used to make the movement. Alternatively, repetitive motion can cause muscle fatigue to exhaustion and stress is on the insertion or origin of the muscular tendon. Repetitive rubbing of the tendon thru a boney canal causes inflammation and therefore, pain thru that area.

Pain is the patient's first warning of an injury. If pain continues, the area will continue to experience damage and swelling will increase. Swelling results in pressure and damage results in bleeding (hemorrhage) which also results in pressure. Pressure and structural damage trigger pain receptors within the tissue.

The physical response to inflammation is pain to the individual. Continued movement of the painful area often results in further injury. Once tissue is injured, it takes longer to heal and may require surgical intervention.

Age can define what kind of damage occurs at a joint. The young tend to receive trauma, fractures, or ligamentous and meniscal injuries. The middle age to older individuals are often struck by arthritis. The most common form of arthritis is osteoarthritis or degenerative joint disease. Arthritis can occur following trauma or an infection of the joint. Arthritis may occur from aging alone. Abnormal anatomy may contribute to early development of osteoarthritis. It is the leading cause of disability in people over the age of 55.

For the person experiencing the pain, it is sometimes difficult to identify the origin of the pain. For example, when a patient has a "sore knee" it can be the whole knee that is in pain. Diagnosis is simpler during the acute phase of an injury as the patient may have been more likely to pinpoint the location of specific pain.

Early identification of the injury frequently narrows down the offending movements sooner and could lead to injury prevention. However, most people, particularly athletes, continue workout and therefore continue to subject the injured area to the offending motion until the pain is more global and affects more of the joint. Unfortunately, by that time other muscle groups are involved and it is more difficult to understand where and what caused the injury.

SUMMARY OF THE INVENTION

The claimed invention provides an appliance for application to the human body for injury prevention, rehabilitation, support, enhance strength, and to improve posture. In one embodiment, the claimed invention may provide an applicator of a relatively elastic material having a first portion for attachment to a first insertion point of a muscle and a second portion for attachment to a second insertion point of the muscle to provide support to the injured muscle.

Other beneficial effects could involve retraining the anatomy to a desired position or away from a non-desired position or prevention of a specific action. The activator will aid in range of motion or stabilizing range of motion to subjects. Such further embodiments could have more than two points of attachment about an injured area.

The claimed invention is comprised of a material with varying degrees of elasticity and will have varying stiffness. The claimed invention may come in a variety of easy to apply shapes. Embodiments of the activator may contain medicinal or herbal ingredients for further treatment of pain and inflammation. Further embodiments may employ electrodes for stimulation of the injured area. Still further embodiments may contain extra supportive structure. Additional embodiments of the claimed invention may include gel-like materials that can be heated or chilled to assist healing.

In the claimed invention, each different shape has a reinforced area or may have tails, limbs, or a combination of both that is used to help anchor the structure to the anatomical area. The purpose of the applicator is to place the strongest or reinforced area of the applicator over the area of pain or over the area requiring support. The claimed invention then provides for the tails of the applicator to be positioned across the skin overlying neighboring anatomical structures. These structures are other tissues, that is, soft tissue, muscle tissue, bone tissue, tendon and ligaments and cartilage that are used to enhance the applicator's effectiveness to perform the desired outcome.

DETAILED DESCRIPTION

Figures 1A, 1B:
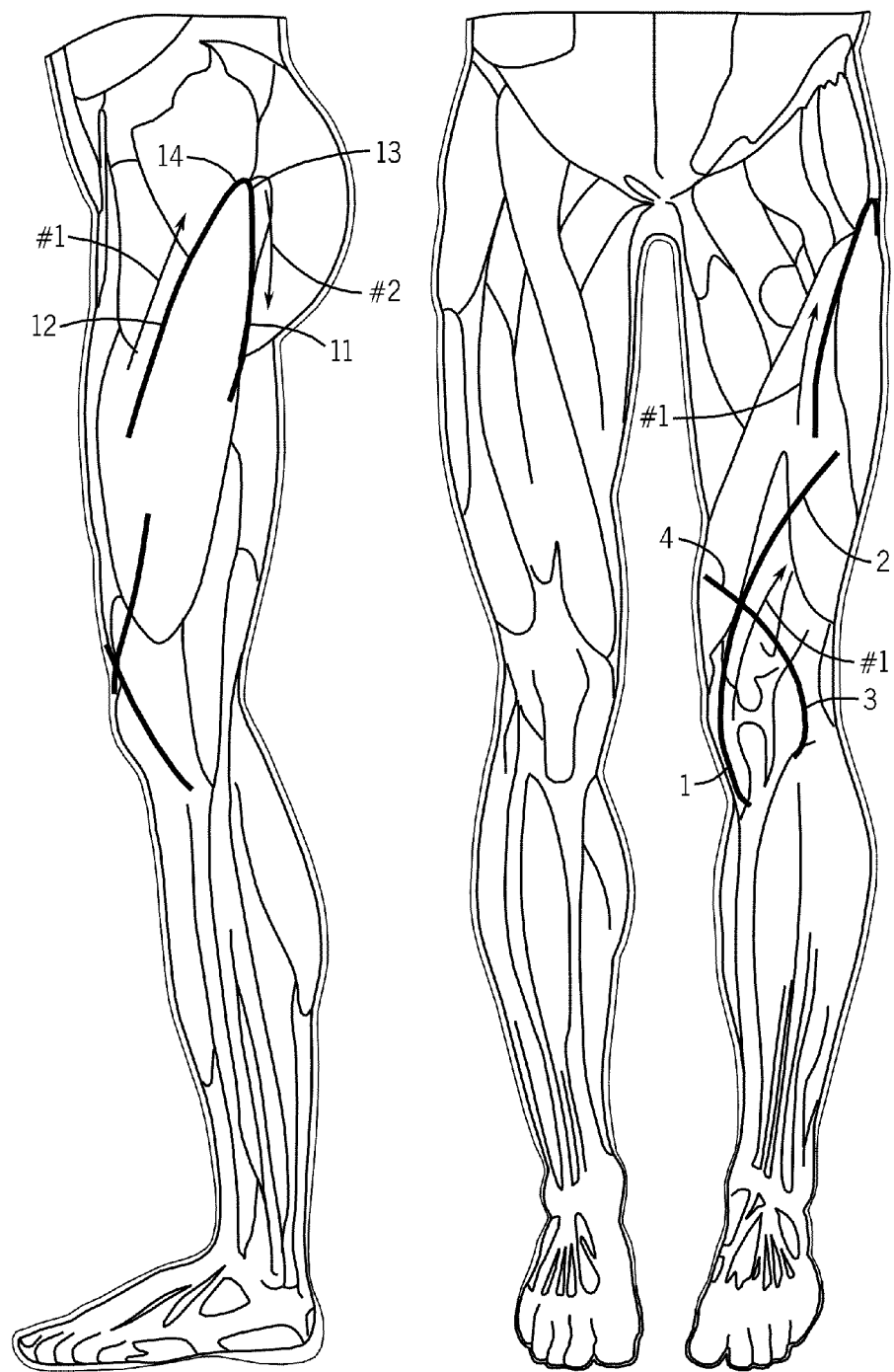
FIG. 1A is a right side elevational view of the human muscular form showing use of the claimed invention to treat a knee injury.
FIG. 1B is front elevational view of the human muscular form showing use of the claimed invention to treat a knee injury.

The claimed activators have been tested by for effectiveness in pain management, range of motion, posture, inflammation reduction, improved circulation, changes in fluid movement and other anatomical changes. The protocol employed diagnostic ultrasound to test the efficacy of the claimed invention as ultrasound permits visualization of muscle and tendon texture, fluid accumulations, blood flow, and bone surfaces. Employing a consistent testing protocol using ultrasound we can identify whether the activators are making a difference within a subjects' anatomy. The following is a summary of the protocol used to test the claimed invention.

Pre Applicator Resting.

Prior to the testing appointment, subjects were asked not to exercise or perform any activity out of the ordinary. Subjects were then asked to report the level of pain that they were experiencing and the level of pain they experience daily using a scale of 1 to 10, with 10 being the worst. The subject's normal activity level, exercise regime and range of motion were recorded. The subject's areas of irritation and pain and the triggers for the pain or discomfort were discussed and recorded. Ultrasound imaging was performed over the areas of interest. As part of the ultrasound studies, measurements of fluid and muscle size were taken. Other potential areas of interest on ultrasound were documented and saved for comparison.

Pre Applicator Post-Exercise

Following ultrasound imaging and discussions the subjects were asked to "aggravate" the injured area with "minimal" activity. Depending on the subject's regular exercise regime, subjects were asked to do about 30% of what they would normally do—usually not more than 15 minutes of exercise, including a warm-up phase. Subjects were then asked to report back to the ultrasound area. The subject's activities were recorded and similar ultrasound images were obtained. Following the ultrasound, applicator(s) were applied to the subjects.

Post Applicator Resting

After approximately one day (24 hrs) of rest, subjects were interviewed for pain level and any further information regarding their injuries. Subjects were tested to evaluate range of motion. Following testing, similar ultrasound images were obtained to compare with the pre-applicator resting images. Additional areas of interest on ultrasound were documented.

Post Applicator Post Exercise

Subjects were then asked to re-aggravate the area by performing the same activity that was performed the day before. Subjects were interviewed to determine their pain level following the activity. Ultrasound images were taken of the area again and measurements are taken This protocol permitted limited control over the subject and provided four data comparison points. The results indicate some variables that are specifically related to the activator usage and provide a basis for understanding the relief of pain or inflammation afforded to the subject.

Trial 1

Trial 1 involved a 53 year old female (Subject 1) with a long history of knee problems including two anterior cruciate ligament repair surgeries and several other several surgeries to excise damaged cartilage. Subject 1 presented with pain most likely due to arthritis associated with her prior surgeries.

Figure 2A:
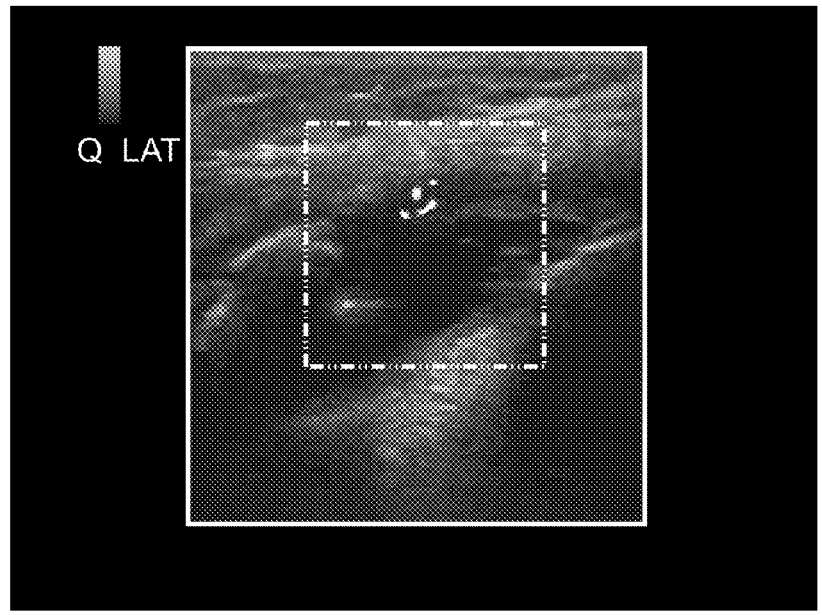
FIG. 2A is an ultrasound image of the knee showing in FIGS. 1A-1C prior to use of an activator using Power Doppler to show blood circulation within the area.
Figure 3A:
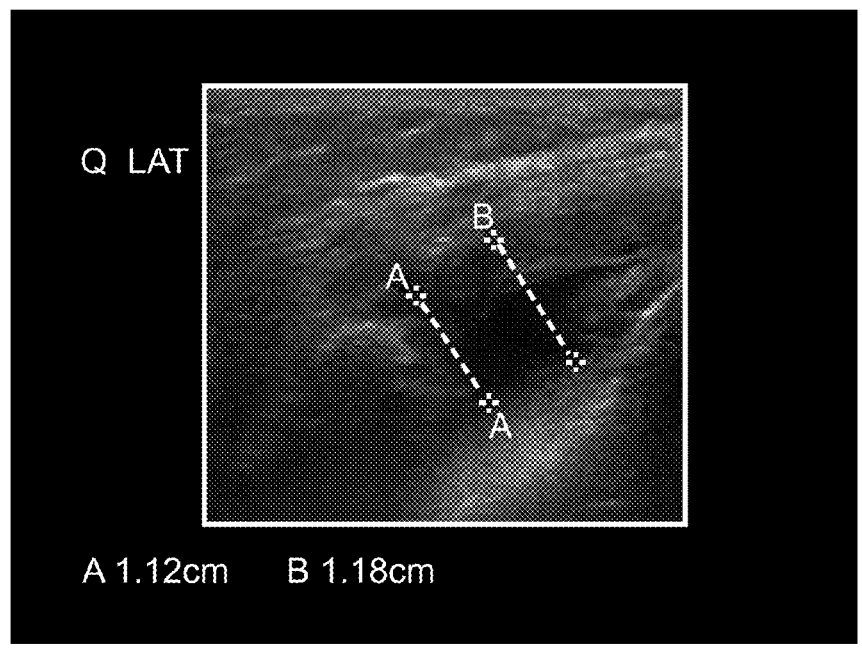
FIG. 3A is an ultrasound image of the knee shown in FIGS. 1A-1C showing significant fluid collection around the joint.

As described above, Subject 1 was asked to avoid extraneous physical activity prior to her appointment. At her appointment, the probable source of pain was identified. Prior to any further testing, diagnostic ultrasound was used to image the area of pain. As shown in FIG. 2A Power Doppler was used to image blood flow through the injured area. Additionally, as shown in FIG. 3A, ultrasound was used to observe a large collection of fluid, synovitis, resulting from her arthritic condition. This inflamed area was one of the likely causes of pain in the subject because of the extra pressure created on tissue by the swelling. Following the ultrasound the resting phase was complete. Subject 1 was then asked to mildly exercise to aggravate the knee.

Following exercise and ultrasound, the appliance was placed on Subject 1. Subject 1 was fitted with a topographical appliance 6. The appliance 6 was fitted with a first portion 1 starting at approximately the head of the fibia, and proceeding up the medial aspect of the knee to intersection 5 above the patellar tendon. Second portion 2 of the appliance 6 continues upwardly approximating the vastus medialis muscle to the intersection 5 above the patellar tendon. Third portion 3 of appliance 6 begins along the lateral aspect of the knee and follows up the illiotibial tract and continues up the lateral aspect of the knee to the intersection 5. Fourth portion 4 of the appliance 6 continues across the grain of the vastas medialus muscle upon which it is anchored.

Figure 1C:
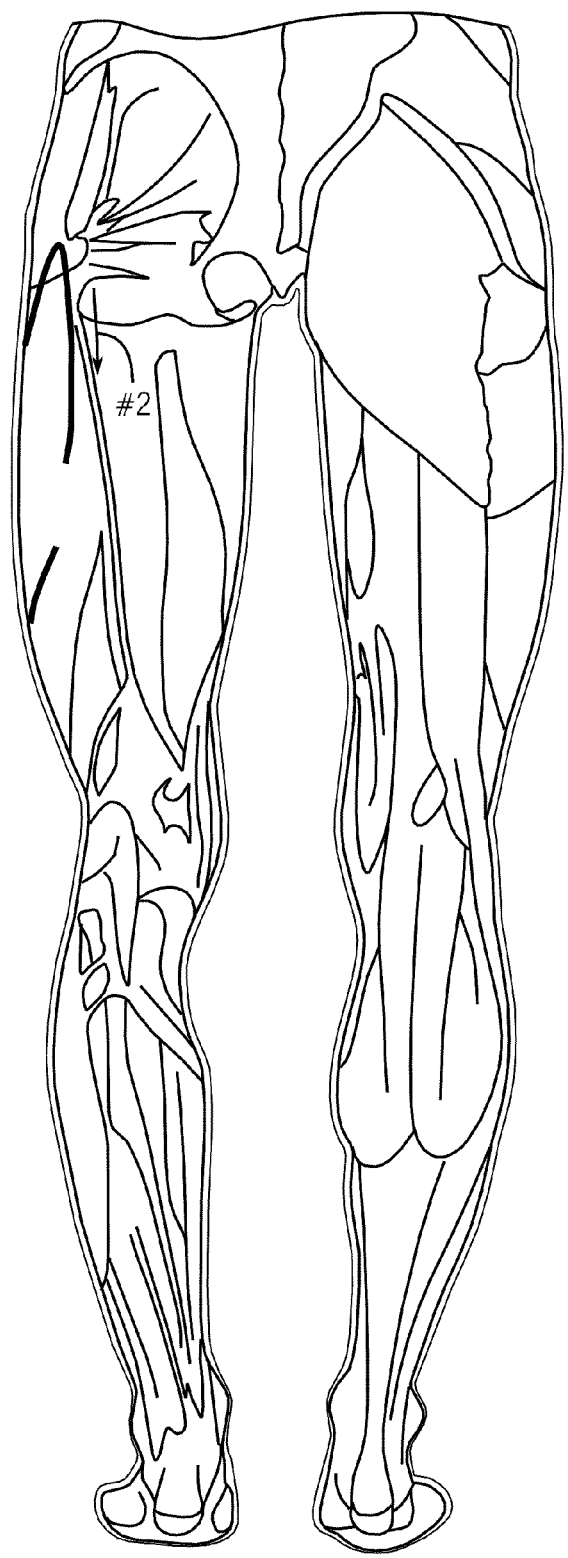
FIG. 1C is a back elevational view of the human muscular form showing use of the claimed invention to treat a knee injury.

As shown in FIGS. 1A-1C, Subject 1 also used a supplemental appliance in the general shape of an inverted V, or chevron 13. The intersection 14 of the chevron 13 is located over the greater trochanter of the femur. The posterior portion 11 of the chevron 13 follows the posterior aspect of the illiotibial tract. The anterior portion 12 of the chevron 13 approximates the anterior aspect of the illiotibial tract.

Figure 2B:
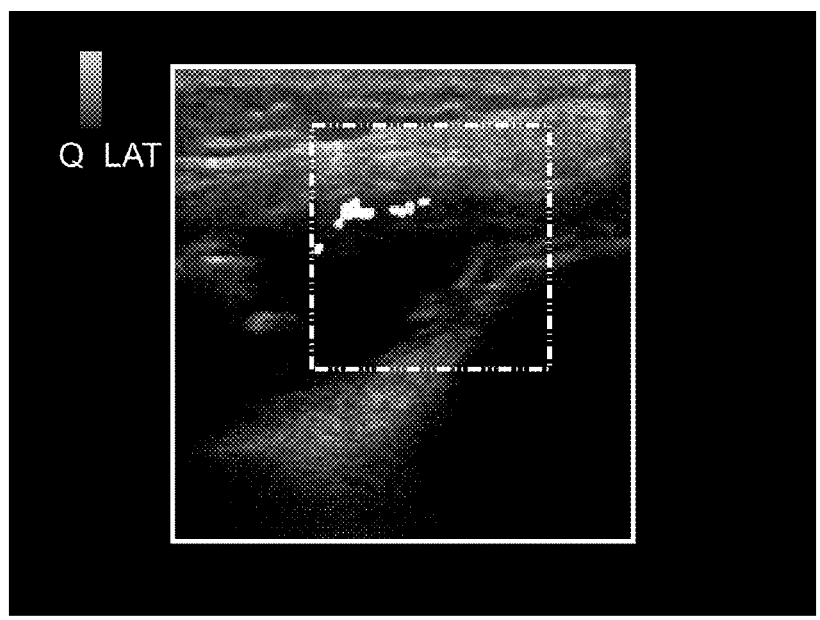
FIG. 2B is an ultrasound imagine of the knee shown in FIG. 2A one day after application of the claimed invention using Power Doppler to show blood circulation within the area.
Figure 3B:
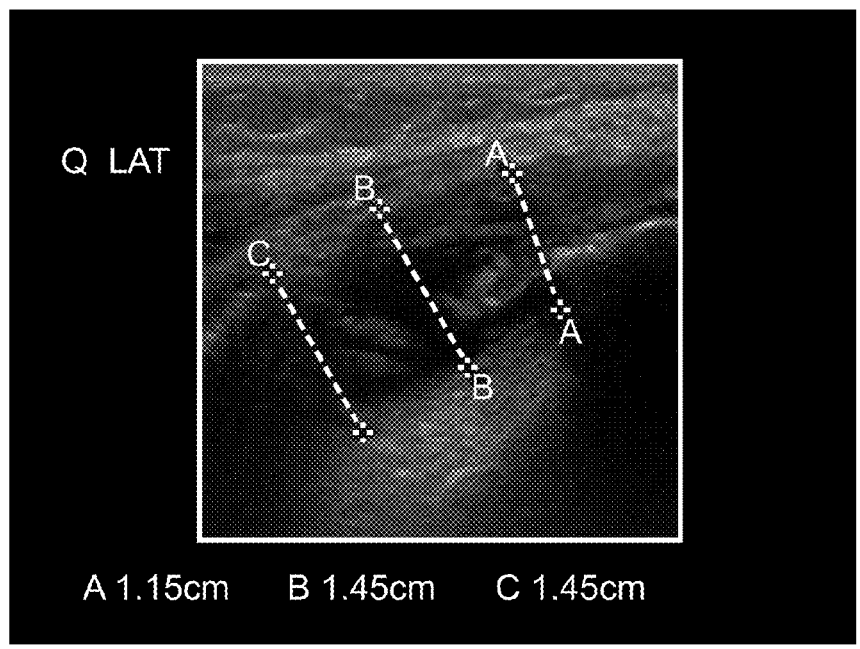
FIG. 3B is an ultrasound image of the knee shown in FIGS. 1A-1C one day after application of the claimed invention.

Subject 1 was then asked to do a brief period of exercise to aggravate her condition and sent home. One day later, the subject returned for additional ultrasound. As shown in FIG. 2B, ultrasound over previous area of pain revealed increased blood circulation following twenty-four hours of wearing the applicator. As shown in FIG. 3B, under ultrasound, it can be observed that the area of fluid elongates. At the same time, upon interview, Subject 1 indicates that she is experiencing less pain.

Trial 2

Trial 2 involved a 78 year old male with a two-year-old injury to his right shoulder ("Subject 2"). Subject 2 had undergone some physical therapy and kinesio-taping but the kinesio-taping had never been consistently applied. As described above, Subject 2 was asked to avoid strenuous activity prior to his appointment.

During his appointment, Subject 2 was imaged using ultrasound, again using Power Doppler to image bloodflow in the injured area. Subject 2 was a very slight individual and points of pain were readily identifiable on both the anterior and posterior aspects of the shoulder. Following the ultrasound, two overlapping cross-type appliances were applied to Subject 2 over the anterior and posterior points of pain.

Figure 4A:
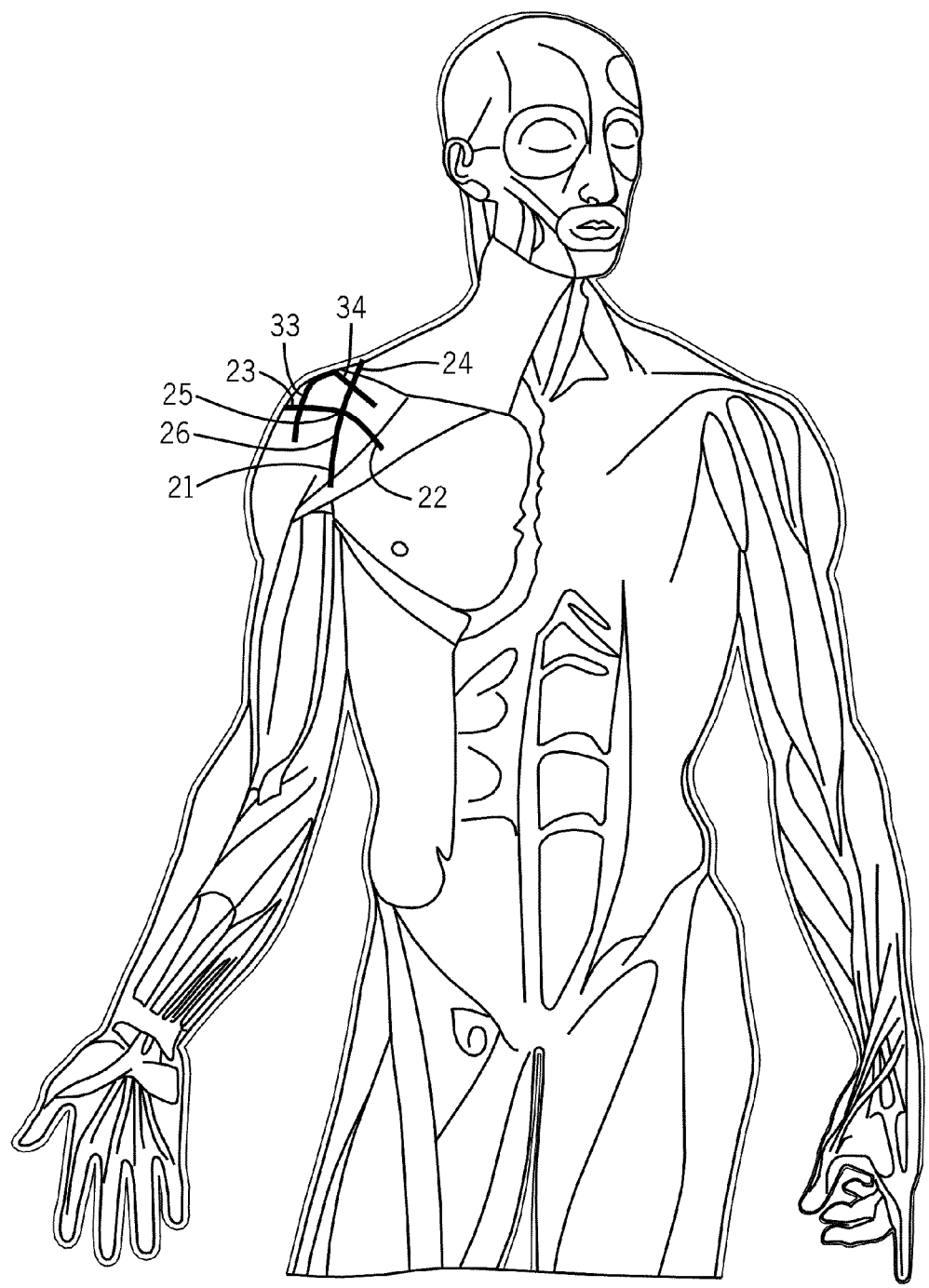
FIG. 4A is a front elevational view of the human muscular form showing use of the claimed invention used to treat a shoulder injury.

As shown in FIG. 4, a first X-shaped shoulder appliance 26 was applied with the intersection 25 of the appliance 26 over the anterior point of pain. The first portion 21 of the appliance 26 proceeds toward the head of the biceps brachii to offer support while the second portion 22 anchors the appliance 26 to the pectoralis major. The third portion 23 of the appliance runs generally across the muscle fibers of the deltoid muscle. The fourth portion 24 of the appliance 26 runs across the clavicle and is anchored on the trapezius muscle.

Figure 4B:
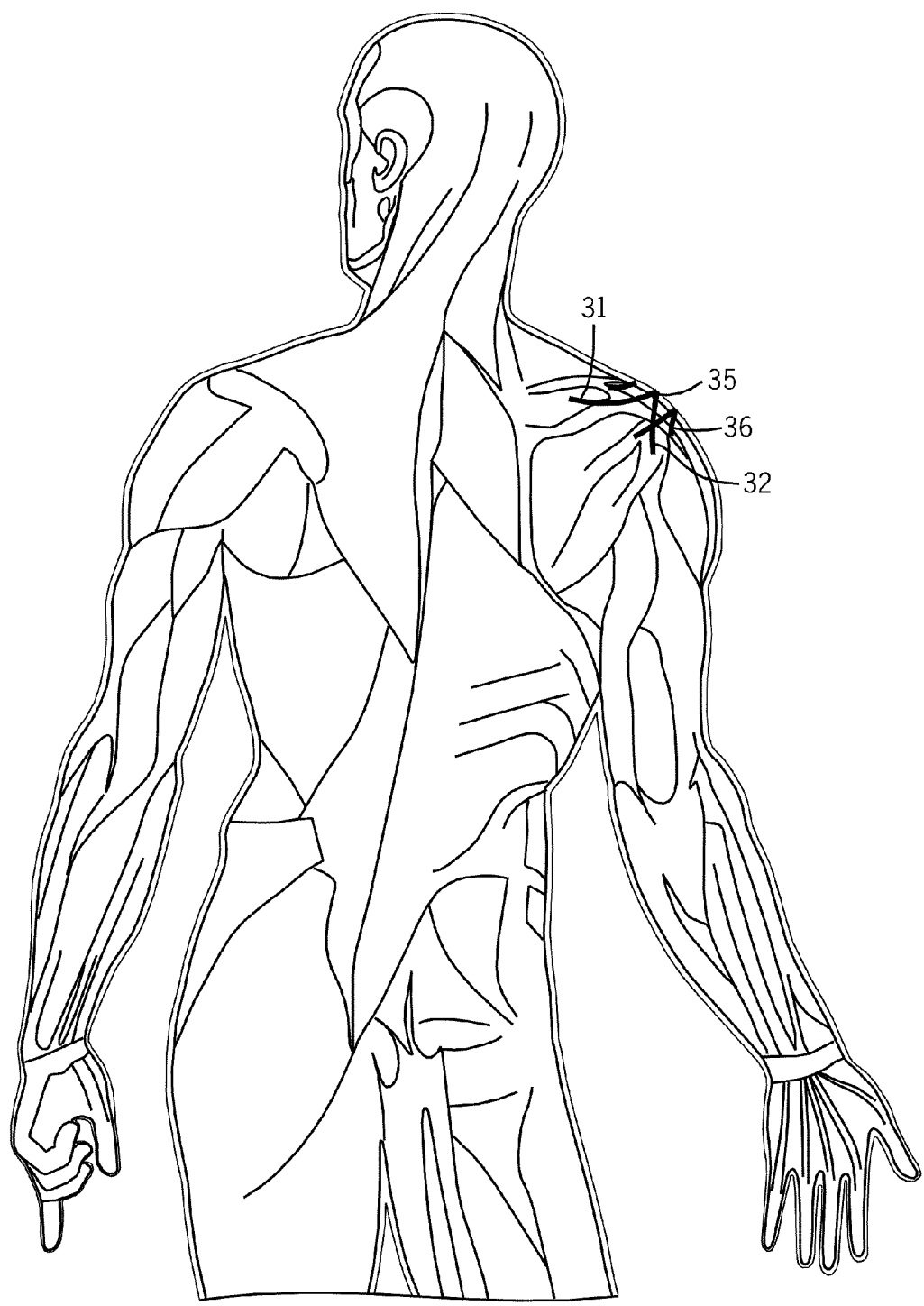
FIG. 4B is a back elevational view of the human muscular form showing use of the claimed invention used to treat a shoulder injury.

As shown in more detail in FIG. 4B, a second X-shaped shoulder appliance 36 was applied with the intersection 35 of the appliance 36 over the posterior point of pain. The first portion 31 of the appliance 36 approximates the supraspinatus muscle while the second portion 32 is anchored over the deltoid. The third portion 33 of the appliance 36 is anchored with the grain of the anterior portion of the deltoid muscle, while the fourth portion 34 of the appliance approximates the attachment point of the deltoid to the clavicle. Subject 2 did not perform any aggravating exercise as he had suffered an acute episode on his already chronic shoulder. This application was to study the response of the anatomy to the activator presence.

Figure 5A:
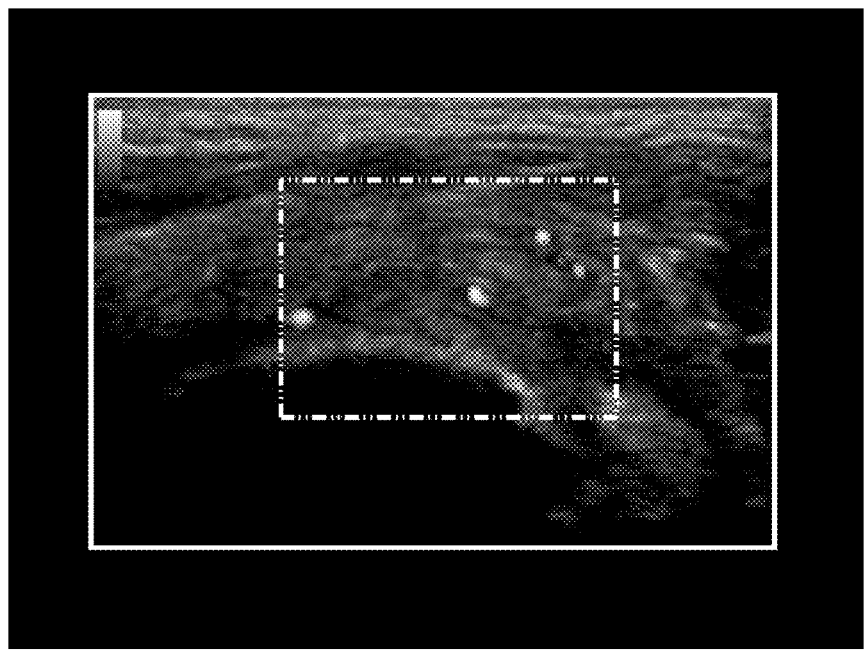
FIG. 5A is an ultrasound image of the shoulder shown in FIGS. 4A-4B prior to use of an activator using Power Doppler to show blood circulation within the area.
Figure 5B:
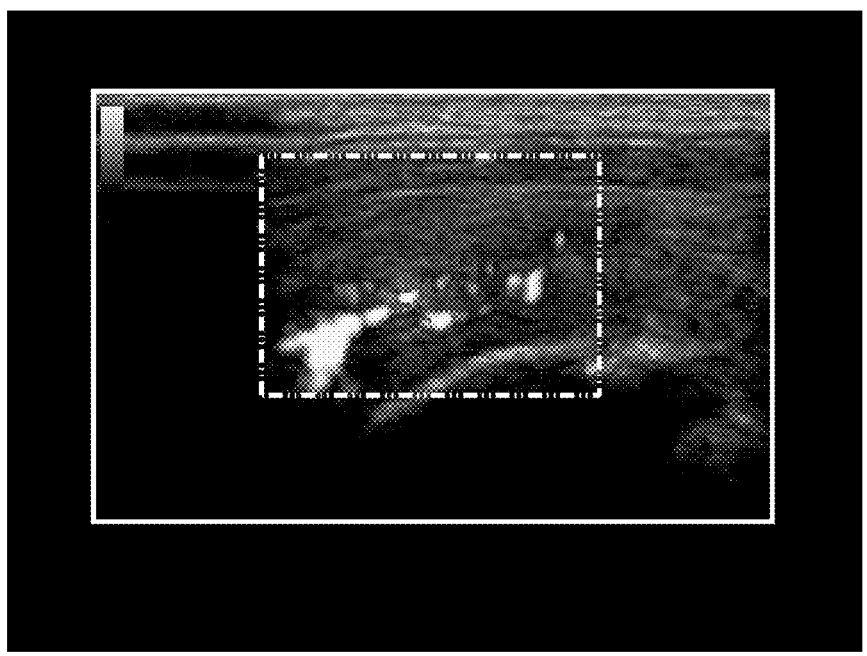
FIG. 5B is an ultrasound image of the shoulder shown in FIG. 4A-4B one day after application of the claimed invention using Power Doppler to show blood circulation within the area.
Figure 6A:
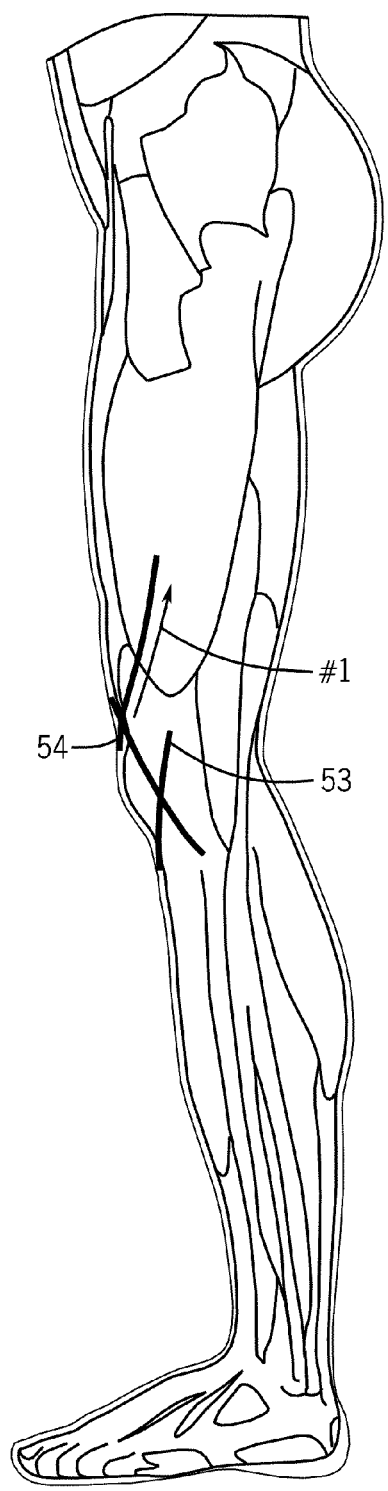
FIG. 6A is a right side elevational view of the human muscular form showing use of the claimed invention to treat a knee injury.
Figure 6B:
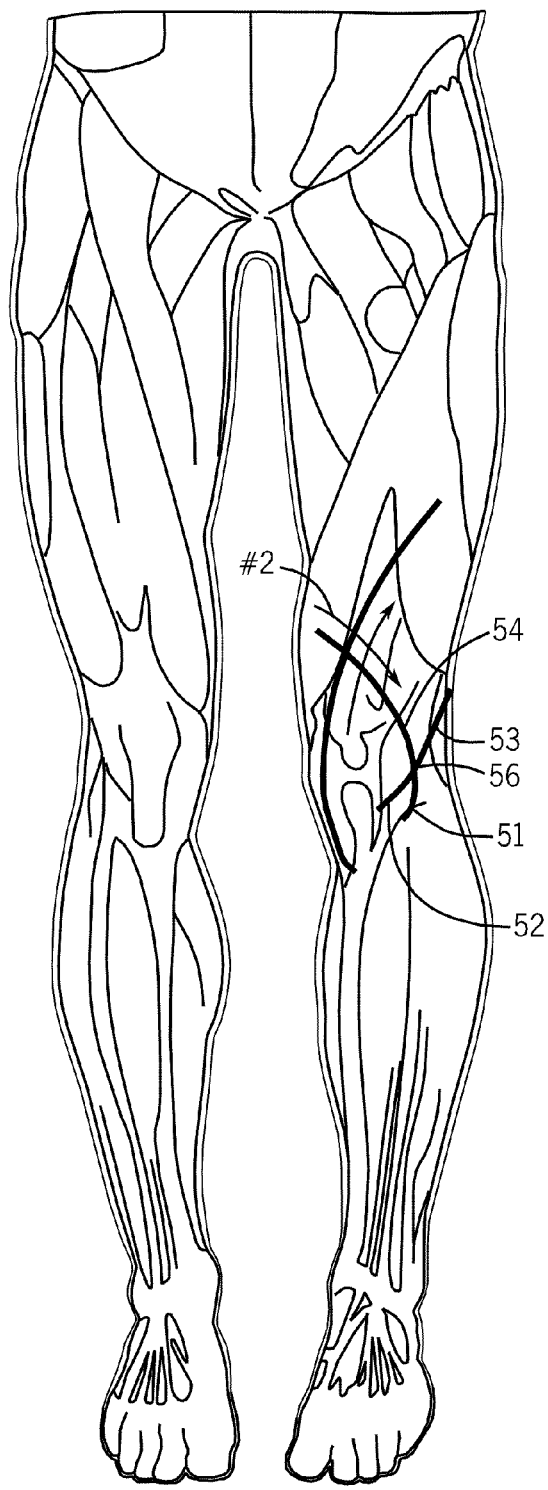
FIG. 6B is front elevational view of the human muscular form showing use of the claimed invention to treat a knee injury.
Figure 6C:
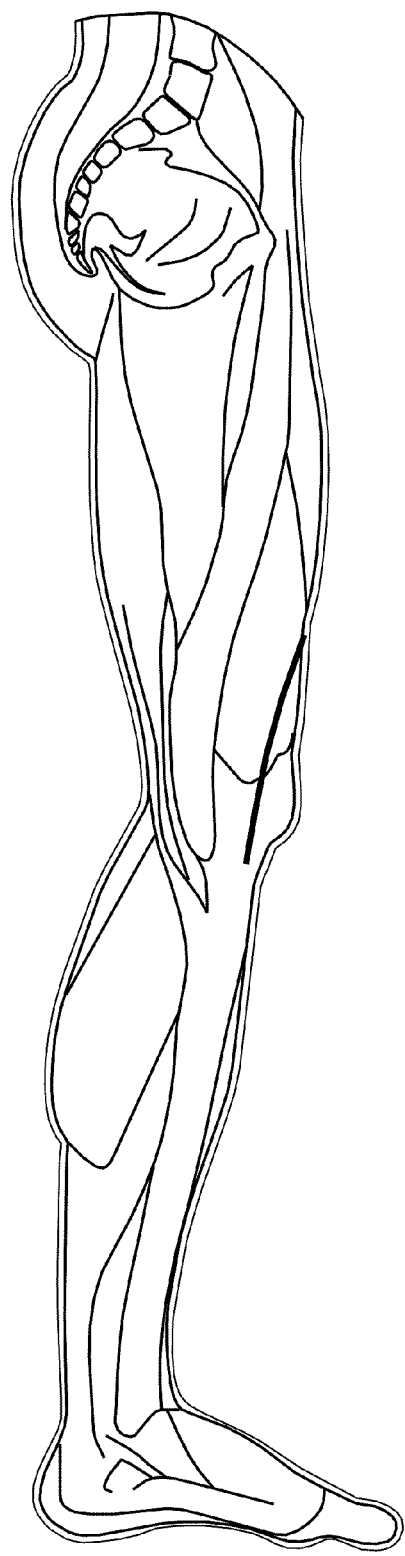
FIG. 6C is a left side elevational view of the human muscular form showing use of the claimed invention to treat a knee injury.

After one day, Subject 2 returned for a second ultrasound study, as shown in FIG. 5B. As can be seen using Power Doppler ultrasound, Subject 2 had significantly more blood flow through the affected area. Additionally, Subject 2 reported less pain.

Trial 3

Figure 7A:
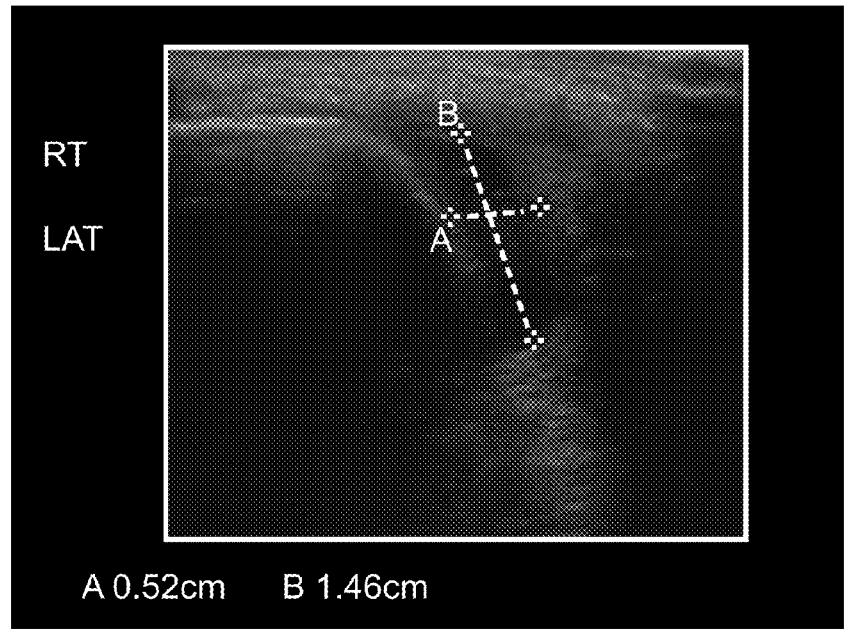
FIG. 7A is an ultrasound image of a knee while resting.
Figure 7B:
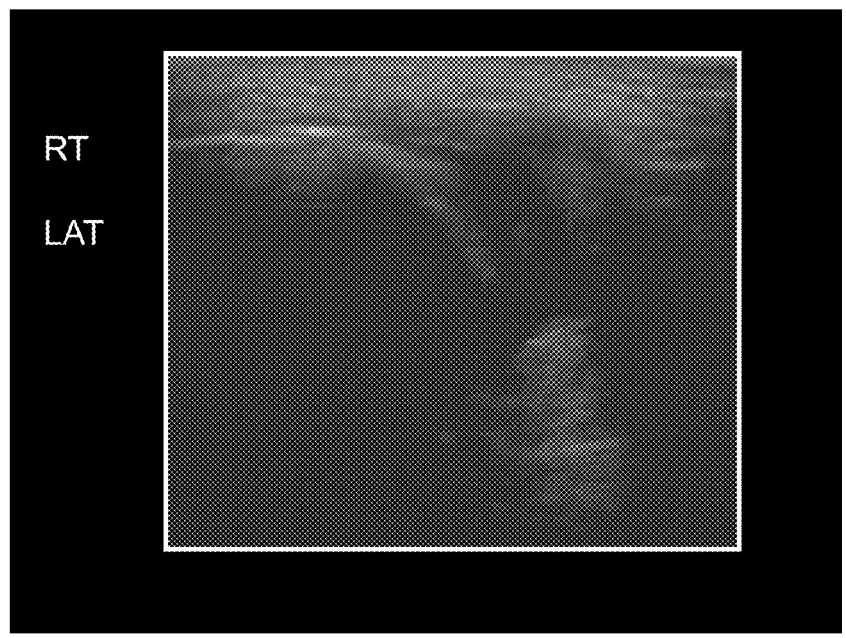
FIG. 7B is an ultrasound image of the knee shown in FIG. 12A prior to exercise.

Trial 3 involved a 38 year old female ("Subject 3") with an extensive running history. Subject 3 formerly ran approximately 5 miles per day but is now pain limited to between 2 and 3 miles per day. Subject 3 complained of "grinding" in her knee during flexion and extension. As discussed above, Subject 3 was asked not to engage in strenuous activity prior to her appointment. As shown in her initial ultrasound in FIG. 7A, there is debris shown in the fluid pocket prior to exercises. FIG. 7B shows a posterior view prior to application of an activator which provides a better aspect of the debris within the fluid.

Figure 7C:
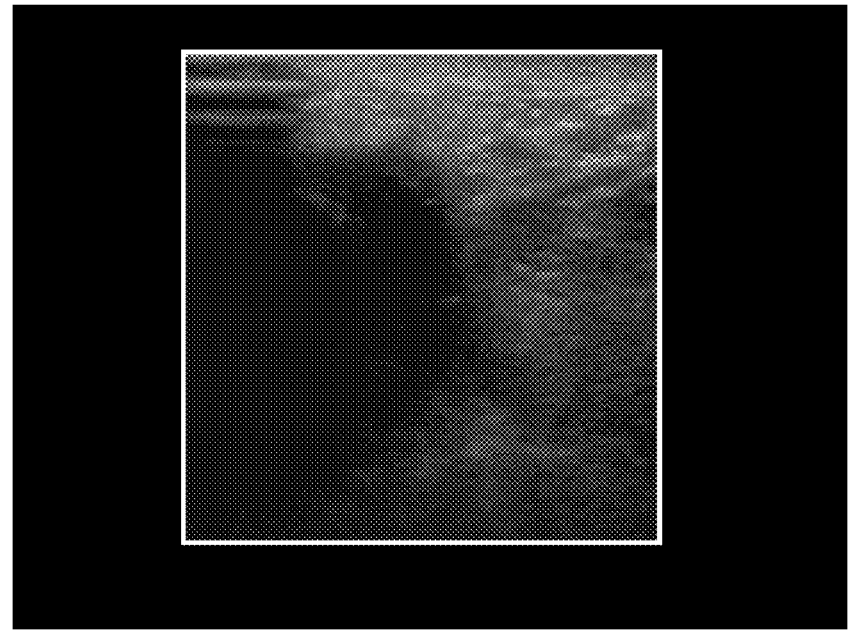
FIG. 7C is an ultrasound image of the knee shown in FIG. 12A following exercise.

In contrast to the Trials 1 and 2, The subject was asked to perform some light exercise to aggravate her condition and then imaged again using ultrasound. As is shown in FIG. 7C, the debris within the fluid is free moving, floating and reflective. Also, there is more fluid following the brief exercise than there was prior to any exercise.

Following the above, two appliances were applied to Subject 3, a larger appliance 46 for overall knee stability and a smaller appliance 56 for lateral stability. Application of the larger appliance 46 is identical to that shown in FIG. 1B and described in more detail above. Smaller appliance 56 is an X-type appliance having a first portion 51 that begins along the lateral aspect of the knee in the lower iliotibial tract and continues upwardly to intersection 55. Second portion 52 is anchored under the patella along the patellar ligament and rises upwardly around lateral aspect of the patella to the intersection 55. Third portion 53 of the appliance starts from the intersection 55 and moves upwardly along the lateral aspect of the biceps femoris. Fourth portion 54 of the appliance starts from the intersection 55 and moves upwardly along the vastus lateralis.

Figure 7D:
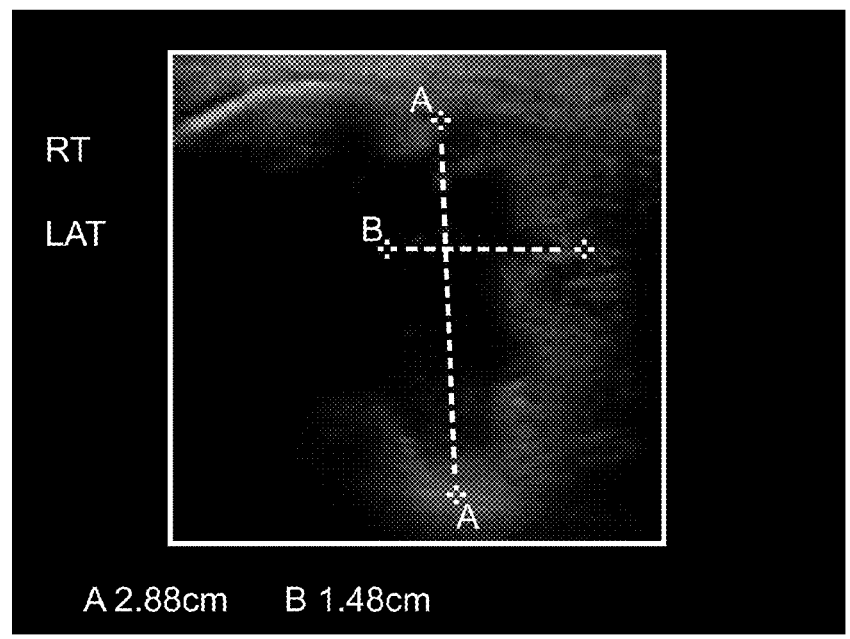
FIG. 7D is an ultrasound image of the knee shown in FIG. 12A following application of an activator.
Figure 7E:
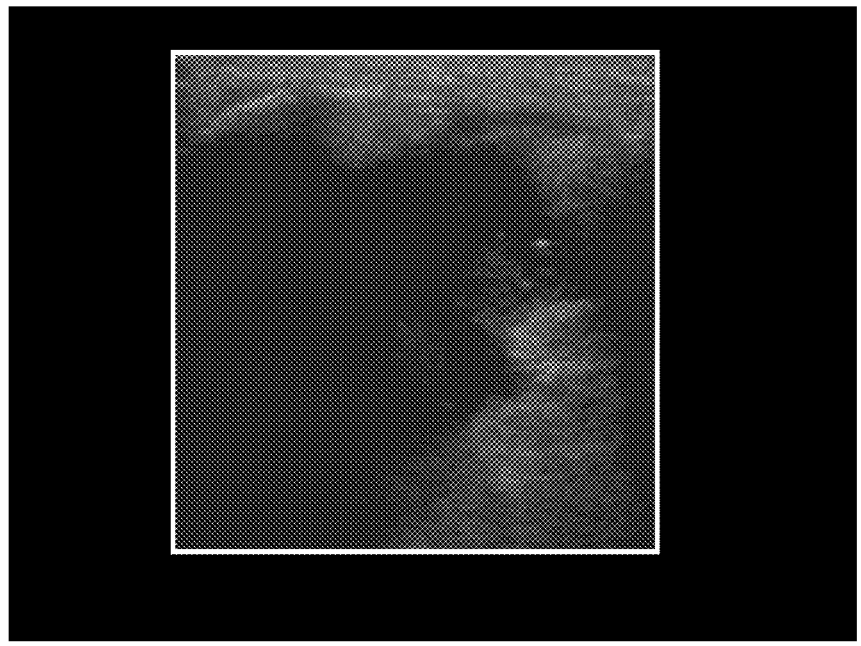
FIG. 7E is an ultrasound image of the knee shown in FIG. 12A one day after application of the activator.
Figure 7F:
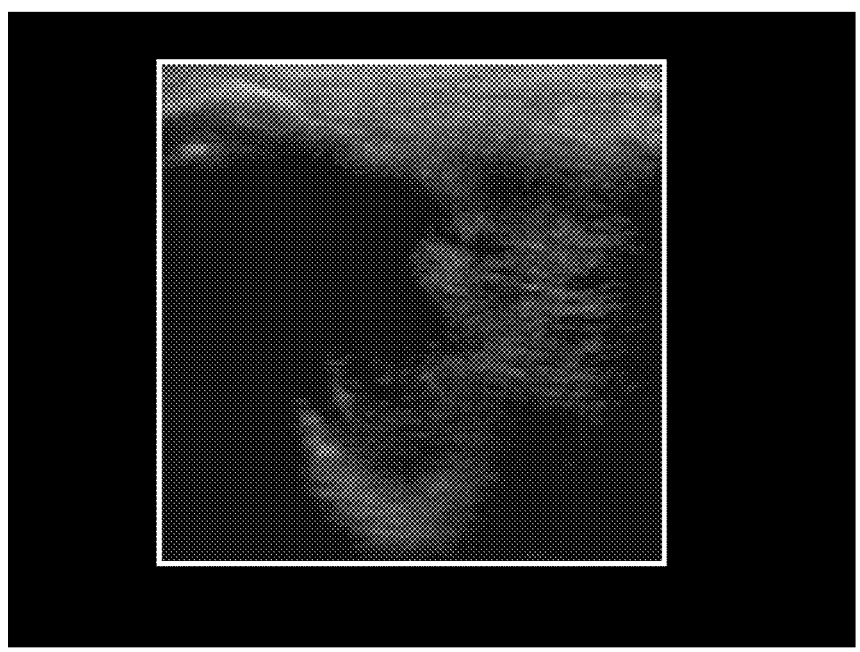
FIG. 7F is an ultrasound image of the knee shown in FIG. 12A two days after application of the activator.
Figure 7G:
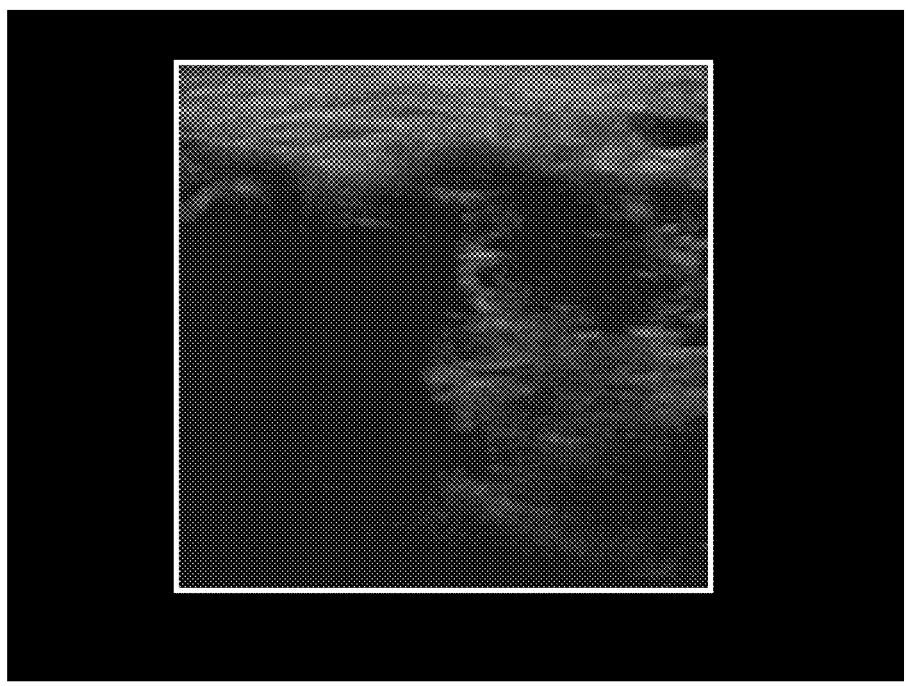
FIG. 7G is a slightly different view of an ultrasound image of the knee shown in FIG. 12A two days after application of the activator.

After one day, Subject 3 returned for ultrasound testing. As shown in FIG. 7D, there is reduced evidence of debris floating in the inflamed area, indicating a change in the density of the particles. One day later, as shown in FIG. 7E, there appears to be still less debris floating within the fluid, but the borders of the fluid appear to have more irregular edges that previously observed. After minimal exercise, Subject 3 was rescanned. This additional scan, shown in FIG. 7F shows a change in the position of debris, that is the debris has settled into the surrounding tissue.

As discussed in some detail above, depending on the desired performance or effect, the appliance is applied using the underlying structures/tissues (soft tissue, muscle tissue, bone tissue, tendon and ligaments and cartilage as the guide or map to reinforce the joint or musculature as an exoskeleton for that joint, musculature or anatomical area. Tissues that are stable and uninjured may be used to reinforce the applicator in a supportive role while the tissue that is injured is also reinforced to prevent further injury. The applicator may also be applied to enhance movement or help prevent movement.

Applicators of different shapes and sizes are created for different injuries such that a specific applicator can be created for several different types of injuries. The applicators are both generic and specific. The applicator shape is also created for different and specific anatomical areas. Other applicators may be placed on other areas of the body to help stabilize the injured or needed area. In the case of an injured joint such as a knee which requires additional support or rehabilitation the hip may be called on for further stabilization. No movement occurs at only one joint or anatomical area) and therefore it is necessary to prevent injury in other areas of the body while another area is weakened or in a healing state. Antagonistic muscle groups may also require stabilization as they can be at risk of injury while the opposite muscle group has been injured or weakened. Any other muscle group or area of the anatomy may require stabilization or support aside from the actual painful area.

Numerous alternative embodiments of the appliance are possible. Among those envisioned include applicators that have at least one point of attachment on one muscle and extend to a second point of attachment on the bone the muscle operates to move when the muscle is flexed. Such an appliance can support the muscle and prevent hyperextension of the muscle. Alternative embodiments may be muscle to muscle to constrict the motion of joint or may approximate bones immediately below the surface to limit joint mobility. Still further embodiments may traverse muscles to provide support or pain relief, or both.

The applicator calls on underlying structures for support, reinforcement and stabilization. Adherence to the skin allows the applicator to be in contact with more cutaneous receptors and mechanoreceptors and may actually contribute to the body's awareness of the site. This aspect of the applicator may enhance the proprioception of the wearer. Movement at the site is under more awareness by the wearer of the applicator and undesired movements are quickly hindered as the wearer is aware of the area. The applicator also provides a lift to the surface anatomy, helping to take pressure off of the Pacinian corpuscles (deep pain receptors) and nociceptors which respond to damage to body tissues leading to pain perception. This lifting also aids the movement of fluid (both blood flow and inflammation) into and away from the area for cleansing of toxins which aggravate the area and result in pain, and for bringing the necessary nutrients so needed for the healing process. If the applicator is heated or cooled, thermoreceptors will be called on to aid in healing.

The appliances employed in the claimed invention can be fabricated from a wide variety of materials and adhered to the skin in any number of ways. Potential materials include all kinds of fabrics and rubbers, whether natural and artificial and all types of plastics, and in particular, rigid and semi-rigid plastics. Appliances can be adhered to the body in any number of ways including adhesives, preferably non-allergenic adhesives and via friction adhesives. In either case, appliances are intended to be secured to the injured area via one of the many known adhesive methods.

Alternatively, the appliances can be integrated into known types of clothing such as compression garments that hold the appliance firmly in place against the injured area. In order to avoid unwanted effects, such garments should be seamless, where possible. The appliances can be integrated into garments in one of any number of known ways.

Whether applied with an adhesive or as part of a garment, the appliances of the claimed invention are designed to both address pain and promote the body's ability to heal itself. The contact of the appliances with the skin increases stimulates the nerve receptors in the area thereby increasing the subject's awareness of the area. Additionally, the supportive nature of the appliances provides proprioreceptive feedback to the wearer. Further embodiments of the claimed invention may essentially serve as exoskeletal support for injured muscles.

Additional embodiments of the activator may contain medicinal/herbal ingredients. Further embodiments may contain extra supportive structure. Additional embodiments of the claimed invention may include gel-like materials that can be heated or chilled to assist healing.

In summary, the claimed appliances can be applied to a muscle or joint to prevent injury, to rehabilitate and injury, to provide support a muscle or joint, to prevent injuries decrease inflammation, retrain muscle memory, to improve posture, or any combination of the above. These appliances create a "flexible exoskeleton" over areas requiring support and/or a mechanical lift to areas requiring rehabilitation, healing, injury prevention to help the body increase oxygen and blood flow to the area and relieve the area of inflammation, toxic build up of waste materials from the body.

What is claimed is:

1. An appliance for topographical application to skin, the appliance comprising:
a continuous elastic material contoured for application to an affected area, the elastic material comprising:
a central intersection portion adapted to be secured to the skin over an injured area;
a first portion and a second portion attached to the central intersection portion to reinforce the intersection portion, the first portion and the second portion adapted to be secured to the affected area adjacent to the injured area to secure the central intersection portion to the skin over the injured area; and
an adhesive material being applied to all of one side of the elastic material;
wherein the adhesive material is adapted to secure the entire one side of the elastic material of the appliance to the skin;
wherein no portion of the central intersection portion, the first portion or the second portion overlaps any other portion while the appliance is secured to the skin; and
wherein each of the portions of the appliance is adapted to provide lift to surface anatomy beneath the skin, the intersection portion providing the strongest lift because of the reinforcement provided by the first and second portions to the intersection portion;
wherein the appliance comprises a material adapted to retain heat or cold for additional rehabilitive effects.

2. The appliance of claim 1 wherein the elastic material further comprises a third portion attached to the central intersection portion, the third portion adapted to be secured to the affected area adjacent to the injured area to secure the central intersection portion to the skin over the injured area.

3. The appliance of claim 2 wherein the elastic material further comprises a fourth portion attached to the central intersection portion, the fourth portion adapted to be secured to the affected area adjacent to the injured area to secure the central intersection portion to the skin over the injured area.

4. The appliance of claim 1 wherein the appliance is adhered such that each portion is adapted to impart tension on the skin.

5. The appliance of claim 1 wherein the elastic material is adapted to include electrodes.

6. An appliance for topographical application to an injured area, the appliance adapted to provide a proprioreceptive and rehabilitative effect to the injured area, to relieve pain, to reduce inflammation, and to provide support and stability to the injured knee, the appliance comprising:
a continuous elastic material contoured for application to the injured area, the elastic material comprising:
an intersection portion adapted to be secured to the skin generally over the patellar tendon;
a first portion attached to the intersection portion, the first portion being adapted to be secured between generally the head of the fibia and the intersection portion along the medial aspect of the knee, the first portion approximates the gracillis tendon;
a second portion attached to the intersection portion, the second portion being adapted to be secured opposite the first portion relative to the intersection portion, the second portion approximating the lateral edge of the vastus medialis muscle;
a third portion attached to the intersection portion, the third portion being adapted to be secured generally along the lateral aspect of the knee and along the illiotibial tract;
a fourth portion attached to the intersection portion, the fourth portion being adapted to be secured across the grain of the vastas medialis muscle; and
an adhesive material being applied to all of one side of the elastic material,
wherein the adhesive material is adapted to secure the entire one side of the appliance to the skin; and
wherein the first, second, third, and fourth portions reinforce the intersection portion and are adapted to secure the central intersection portion to the skin over the patellar tendon;
wherein none of the portions of the appliance overlaps any other portion while the appliance is secured to the skin;
wherein each of the portions of the appliance is adapted to provide lift to surface anatomy beneath the skin, the intersection portion over the patellar tendon providing the strongest lift because of the reinforcement provided by the first, second, third, and fourth portions to the intersection portion;
wherein the appliance comprises a material adapted to retain heat or cold for additional rehabilitive effects.

7. The appliance of claim 6 wherein the appliance further comprises at least one topically administered medication to reduce pain or inflammation.

8. An appliance for topographical application to an injured area, the appliance adapted to provide a proprioreceptive and rehabilitative effect to the injured area, to relieve pain, to reduce inflammation, and to provide support and stability to the area, the appliance comprising:
a continuous elastic material contoured for application to the injured area, the elastic material comprising:
an intersection portion being adapted to be secured to the skin generally over the greater trochanter of the femur;

a first portion attached to the intersection portion, the first portion being adapted to be secured generally along the posterior aspect of the illiotibial tract;

a second portion attached to the intersection portion, the second portion being adapted to be secured generally along the anterior aspect of the illiotibial tract; and an adhesive material being applied to all of one side of the elastic material, wherein the adhesive material is adapted to secure the entire one side of the appliance to the skin; and wherein no portion of the intersection portion, the first portion, or the second portion overlaps any other portion while the appliance is secured to the skin;

wherein the first and second portions reinforce the intersection portion and are adapted to secure the central intersection portion to the skin over the greater trochanter of the femur;

wherein each of the portions of the appliance is adapted to provide lift to surface anatomy beneath the skin over the each of the skin, the intersection portion over the greater trochanter of the femur providing the strongest lift because of the reinforcement provided by the first and second portions to the intersection portion;

wherein the appliance comprises a material adapted to retain heat or cold for additional rehabilitive effects.

9. The appliance of claim 8 wherein the appliance further comprises at least one topically administered medication to reduce pain or inflammation.

* * * * *